US011345651B2

(12) United States Patent
Tsuchiya et al.

(10) Patent No.: US 11,345,651 B2
(45) Date of Patent: *May 31, 2022

(54) ADDITION CONDENSATION PRODUCT, PRODUCTION METHOD AND USE OF SAME, POLYMERIZATION VESSEL, AND PRODUCTION METHOD OF POLYMER

(71) Applicant: Shin-Etsu Chemical Co., Ltd., Kamisu (JP)

(72) Inventors: Yoshikatsu Tsuchiya, Kamisu (JP); Kentaro Yamanaka, Kamisu (JP); Masahiro Usuki, Kamisu (JP)

(73) Assignee: Shin-Etsu Chemical Co., Ltd., Kamisu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/336,854

(22) Filed: Jun. 2, 2021

(65) Prior Publication Data

US 2021/0403405 A1 Dec. 30, 2021

(30) Foreign Application Priority Data

Jun. 29, 2020 (JP) .............................. JP2020-111136
Jan. 15, 2021 (JP) .............................. JP2021-004690

(51) Int. Cl.
*C07C 47/546* (2006.01)
*C08G 16/02* (2006.01)
*C08K 5/07* (2006.01)
*C08F 2/00* (2006.01)

(52) U.S. Cl.
CPC ............ *C07C 47/546* (2013.01); *C08F 2/004* (2013.01); *C08G 16/0225* (2013.01); *C08K 5/07* (2013.01); *C07C 2602/10* (2017.05)

(58) Field of Classification Search
CPC ............ C08G 16/0225; C08G 16/0231; C07C 47/546; C07C 2602/10; C08K 5/07; C08F 2/004

See application file for complete search history.

(56) References Cited

U.S. PATENT DOCUMENTS

| 5,508,361 A | * 4/1996 | Shimizu ................. C08F 10/00 526/62 |
| 6,022,932 A | 2/2000 | Ooura et al. |
| 6,121,390 A | * 9/2000 | Shimizu ................. C08F 2/004 526/62 |
| 6,335,403 B1 | * 1/2002 | Shimizu ................. C08F 2/004 526/346 |
| 6,355,743 B1 | 3/2002 | Ooura et al. |
| 6,906,129 B2 | * 6/2005 | Watanabe ................ C08F 2/00 524/593 |
| 6,906,149 B2 | * 6/2005 | Watanabe ................ C08F 2/00 526/317.1 |
| 2005/0054789 A1 | 3/2005 | Watanabe et al. |
| 2010/0261854 A1 | * 10/2010 | Watanabe .......... C08G 16/0225 526/62 |

FOREIGN PATENT DOCUMENTS

| JP | H10-095804 A | 4/1998 |
| JP | 2005-048024 A | 2/2005 |
| JP | 2005-097601 A | 4/2005 |
| JP | 5445142 B2 | 3/2014 |

OTHER PUBLICATIONS

7--,.

* cited by examiner

*Primary Examiner* — Karuna P Reddy
(74) *Attorney, Agent, or Firm* — Oblon, McClelland, Maier & Neustadt, L.L.P.

(57) ABSTRACT

Provided is an addition condensation product of an aromatic compound and a carbonyl compound. The addition condensation product includes an aromatic compound dimer in which two composition units derived from the aromatic compounds are bonded via one composition unit derived from the carbonyl compound and an aromatic compound multimer in which each of three or more composition units derived from the aromatic compounds is bonded via one composition unit derived from the carbonyl compound. A ratio of the aromatic compound dimer to the aromatic compound multimer is in the range of 1:75 to 1:1,000.

20 Claims, 1 Drawing Sheet

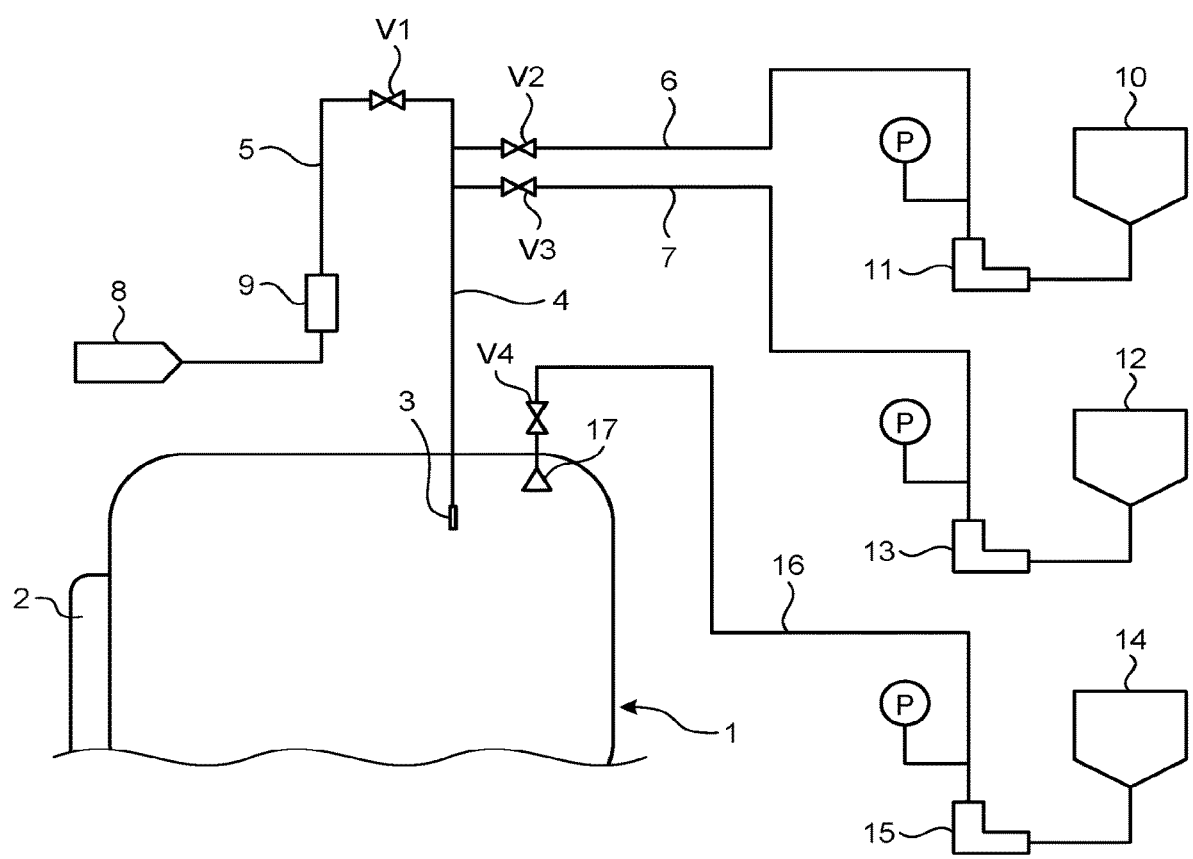

ADDITION CONDENSATION PRODUCT, PRODUCTION METHOD AND USE OF SAME, POLYMERIZATION VESSEL, AND PRODUCTION METHOD OF POLYMER

CROSS-REFERENCE TO RELATED APPLICATION(S)

The present application claims priority to and incorporates by reference the entire contents of Japanese Patent Application No. 2020-111136 filed in Japan on Jun. 29, 2020 and Japanese Patent Application No. 2021-004690 filed in Japan on Jan. 15, 2021.

BACKGROUND OF THE INVENTION

1. Field of the Invention

The present invention relates to a polymer scale adhesion preventive agent, a polymerization vessel, a production method of the polymer scale adhesion preventive agent, and a production method of a polymer, especially to: a polymer scale adhesion preventive agent that has a property of preventing a polymer scale from adhering to an inner wall surface and the like of a polymerization vessel upon producing a polymer by polymerizing a monomer having an ethylenic double bond in a polymerization vessel; a polymerization vessel that is coated with the polymer scale adhesion preventive agent; a production method of the polymer scale adhesion preventive agent; and a production method of a polymer.

2. Description of the Related Art

It has been known that, upon polymerizing a monomer having an ethylenic double bond, the polymer thereby formed adheres to an inner wall surface and the like of a polymerization vessel as a scale. Adhesion of this polymer scale becomes eminent as the polymerization batch number is increased thereby leading to decrease in a yield of the polymer, a cooling capacity of the polymerization vessel, and the like. In addition, there is a problem in that the polymer scale that is detached from the inner wall surface and the like of the polymerization vessel contaminates the obtained polymer thereby resulting in deterioration of the product quality. On top of these problems, not only the removing work of the polymer scale that adheres to the inner wall surface and the like of the polymerization vessel requires excessive working load and time, but also there is a danger that an unreacted monomer included in the polymer scale may cause a harm to a human body.

Conventionally, when the monomer having an ethylenic double bond is polymerized, there has been known the method in which in order to prevent the polymer scale from adhering to the inner wall surface and the like of the polymerization vessel, a coating film is formed on the inner wall surface, an agitator, and the like of the polymerization vessel by applying a polymer scale adhesion preventive agent (hereinafter, this is also called "scale preventive agent"). Known examples of the polymer scale adhesion preventive agent include a mixture of a condensation reaction product, which is obtained from a naphthol and a carbonyl compound, with an organic phosphate compound (and a water-soluble dye, in addition) (Japanese Patent No. 5445142).

However, it became apparent that the polymer scale adhesion preventive agent described in Japanese Patent No. 5445142 causes accumulation due to the polymer scale adhesion preventive agent that is adsorbed onto the inner wall surface of the polymerization vessel, a polymerization assisting agent, and an unreacted carbonyl compound as the polymerization batch number gets larger, thereby resulting in an eminent decrease in the overall heat transfer coefficient. Specifically, after about 1,000 batches, the thickness thereof reaches 50 µm and the overall heat transfer coefficient becomes about 15%. When the polymerization batch number is increased to about 1,000 or more, the polymer scale starts to adhere onto an irregular coating film of the polymer scale adhesion preventive agent; then, the adhering polymer scale grows. Then, the growth reaches to the point where the detached scale contaminates the obtained polymer. Therefore, there has been a problem of causing fish eyes in the polymer product.

SUMMARY OF THE INVENTION

The present invention was made in the light of the circumstances mentioned above; thus, an object thereof is to provide: an addition condensation product that can form, as a polymer scale adhesion preventive agent especially for production of a polymer of a monomer having an ethylenic double bond, a coating film capable of achieving prevention of adhesion of a polymer scale onto an inner surface wall and the like of a polymerization vessel thereby increasing productivity of the polymer; a production method of the addition condensation product; a polymerization vessel to which the addition condensation product adheres; and a production method of a polymer.

The inventors of the present invention carried out an extensive investigation to achieve the object mentioned above; as a result, it was found that when as a polymer scale adhesion preventive agent on the inner wall surface of a polymerization vessel for production of a polymer of a monomer having an ethylenic double bond, a solution of an addition condensation product of an aromatic compound and a carbonyl compound described below was applied to form a polymer scale adhesion preventive layer, satisfactory scale adhesion preventive performance could be expressed. It was further found that even when many polymerization batches were repeated, deposition due to the polymer scale adhesion preventive agent, a polymerization assisting agent, and an unreacted carbonyl compound did not occur; thus, the decrease in the overall heat transfer coefficient of a jacket of the polymerization vessel could be effectively prevented. Here, the addition condensation product is characterized in that among the addition condensation products obtained by an addition condensation reaction of the aromatic compound and the carbonyl compound, the ratio of the aromatic compound dimer that is produced by the reaction of the aromatic compound and the carbonyl compound with the mole ratio of 2 to 1 to the aromatic compound trimer or higher in the addition condensation products is in the range of 1:75 to 1:1,000. The present invention could be achieved on the basis of these findings.

Therefore, the present invention provides: the addition condensation product of an aromatic compound and a carbonyl compound described below; a use of the addition condensation product as a polymer scale adhesion preventive agent; a polymerization vessel that is coated with the polymer scale adhesion preventive agent; a production method of the polymer scale adhesion preventive agent; and a production method of a polymer.

A addition condensation product of an aromatic compound and a carbonyl compound according to one aspect of the present invention includes an aromatic compound dimer in which two composition units derived from the aromatic compounds are bonded via one composition unit derived from the carbonyl compound; and an aromatic compound multimer in which each of three or more composition units derived from the aromatic compounds is bonded via one composition unit derived from the carbonyl compound, wherein a ratio of the aromatic compound dimer to the aromatic compound multimer is in a range of 1:75 to 1:1,000.

According to another aspect of the present invention, in the addition condensation product, it is preferable that the aromatic compound is a naphthol.

According to still another aspect of the present invention, in the addition condensation product, it is preferable that the carbonyl compound is an aldehyde compound or a ketone compound.

According to still another aspect of the present invention, in the addition condensation product, it is preferable that the aromatic compound is a compound represented by general formula (1) below and the carbonyl compound is an aldehyde compound represented by general formula (2) below:

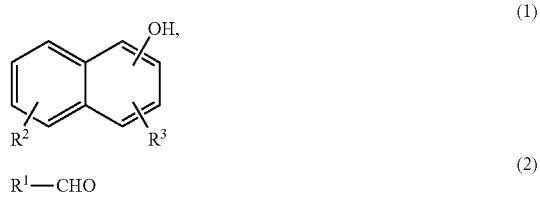

(1)

$R^1$—CHO (2)

(where $R^1$, $R^2$, and $R^3$ each in the general formulae (1) and (2) each represent a hydrogen atom or a hydrocarbon group).

According to still another aspect of the present invention, in the addition condensation product, it is preferable that the aromatic compound is α-naphthol, and the carbonyl compound is formaldehyde.

A production method of an addition condensation product according to still another aspect of the present invention includes a step at which an aromatic compound, a carbonyl compound, and a catalyst are mixed in a reaction solvent, and an addition condensation reaction of the aromatic compound and the carbonyl compound is conducted to obtain the addition condensation product of the aromatic compound and the carbonyl compound, wherein the addition condensation product includes an aromatic compound dimer in which two composition units derived from the aromatic compounds are bonded via one composition unit derived from the carbonyl compound and an aromatic compound multimer in which each of three or more composition units derived from the aromatic compounds is bonded via one composition unit derived from the carbonyl compound, and a ratio of the aromatic compound dimer to the aromatic compound multimer is in a range of 1:75 to 1:1,000.

According to still another aspect of the present invention, in the production method of an addition condensation product, it is preferable that the aromatic compound is α-naphthol, the carbonyl compound is formaldehyde, and the catalyst is an alkali metal hydroxide.

In a polymerization vessel used in polymerizing a monomer according to still another aspect of the present invention, the addition condensation compound adheres to an inner wall surface of the polymerization vessel to which the monomer contacts.

According to still another aspect of the present invention, the polymerization vessel may be further include a reflux condenser to condense the monomer during polymerization.

According to still another aspect of the present invention, in the polymerization vessel, it is preferable that the monomer is a monomer having an ethylenic unsaturated group.

According to still another aspect of the present invention, in the polymerization vessel, it is preferable that the monomer having an ethylenic unsaturated group is vinyl chloride.

In a production method of a polymer according to still another aspect of the present invention, the monomer is polymerized in the polymerization vessel.

In use of the addition condensation product according to still another aspect of the present invention, the addition condensation product is used as a polymer scale adhesion preventive agent used in polymerizing vinyl chloride or a monomer mixture mainly including vinyl chloride.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWING

FIG. 1 is a schematic diagram illustrating one example of an apparatus with which a solution of the addition condensation product of an aromatic compound and a carbonyl compound according to the present invention is applied.

DETAILED DESCRIPTION OF PREFERRED EMBODIMENTS

Hereinafter, the present invention will be described in more detail.

Addition Condensation Product

The addition condensation product according to the present invention is an addition condensation product of an aromatic compound and a carbonyl compound. This addition condensation product includes an aromatic compound dimer in which two composition units derived from the aromatic compounds are bonded via one composition unit derived from the carbonyl compound and an aromatic compound multimer in which each of three or more composition units derived from the aromatic compounds is bonded via one composition unit derived from the carbonyl compound; and a ratio of the aromatic compound dimer to the aromatic compound multimer is in the range of 1:75 to 1:1,000. The ratio of the aromatic compound dimer to the aromatic compound multimer should be calculated from the ratio of peak areas in a high-performance liquid chromatography. Because the ratio is within the above-mentioned range, use of the addition condensation product as the polymer scale adhesion preventive agent according to the present invention can express a satisfactory scale adhesion preventive performance. In addition, even when many polymerization batches are repeated, deposition due to the polymer scale adhesion preventive agent, a polymerization assisting agent, and an unreacted carbonyl compound does not occur; thus, the decrease in the overall heat transfer coefficient of a jacket of the polymerization vessel can be effectively prevented. Note that the polymer scale adhesion preventive agent described in Japanese Patent No. 5445142 cannot sufficiently express the NS preventive performance.

Specifically, the aromatic compound has a portion that constitutes in the addition condensation product the composition unit (A) that is derived from the aromatic compound. Also, the carbonyl compound has a portion that constitutes in the addition condensation product the composition unit (B) that is derived from the carbonyl compound. In this specification, the aromatic compound dimer means the compound having the A-B-A structure, and the aromatic compound multimer means the compound having the A-B-A- . . . -B-A structure in which "A" and "B" are alternately disposed.

The addition condensation product according to the present invention is usually prepared as a solution that contains the addition condensation product. Specifically, this solution of the addition condensation product is the solution of the addition condensation product that is obtained by mixing an aromatic compound, a carbonyl compound, and a catalyst in a reaction solvent followed by the addition condensation reaction of the aromatic compound with the carbonyl compound. In the solution of the addition condensation product, among the addition condensation products, the ratio of the aromatic compound dimer that is produced by the reaction of the aromatic compound and the carbonyl compound with the mole ratio of 2 to 1 to the aromatic compound trimer or higher in the addition condensation products is in the range of 1:75 to 1:1,000. This ratio is preferably in the range of 1:80 to 1:1,000, and more preferably in the range of 1:80 to 1:500, while still more preferably in the range of 1:80 to 1:400.

The known polymer scale adhesion preventive agent that is used for the two-step application includes a first coating liquid containing a quinone type compound condensation product and a second coating liquid containing a polyphosphate, as disclosed in Japanese Patent Application Laid-open No. 2003-40907. In the production method of the polymer of the monomer having an ethylenic unsaturated double bond by using the polymer scale adhesion preventive agent, which is described in this patent document, the amount of the adhering scale after polymerization is small; but the scale that is adhering during polymerization readily comes off. Accordingly, due to scrape-off of the scale by particles of polyvinylchloride (PVC) that is produced by polymerization, there has been the problem of a rapid increase in the fish eye in some cases.

Aromatic Compound

Specifically, illustrative examples of the aromatic compound include a benzene derivative, a naphthalene derivative, a polynuclear aromatic compound, and a non-benzene type aromatic compound. The number of the conjugative π bond included in the benzene derivative, the naphthalene derivative, the polynuclear aromatic compound, and the non-benzene type aromatic compound is preferably in the range of 3 to 20. These compounds may be used singly or as a combination of two or more of them.

Illustrative examples of the benzene derivative include phenol and its derivatives, such as phenol, 2-methylphenol, 3-methylphenol, 4-methylphenol, and 3,5-dimethylphenol; aromatic amines and their derivatives, such as pyridine, quinoline, carbazole, o-phenanthroline, p-phenanthroline, 3,6-diaminoacridine, 3-aminophenothiazine, 2-aminophenadine, phenothiazine, and 2-hydroxy-4-methylquinoline; nitro- and nitroso-derivatives such as nitrobenzene, phenazine, phenazine oxide, 1-phenylazo-2-naphthol, triphenodioxazine, and 4-nitroxanthone; aromatic aldehydes such as benzaldehyde and benzofuran; benzene derivatives further having one substituent group other than the aldehyde group, such as 1-hydroxy-2,4-methylfluorone, 3-phenyl-cumarone, ethyl cumarine-3-carboxylate, 3-acetylcumarine, 5-chloro-3-(4-hydroxyphenyl)anthranyl, and 3-nitroacridone; benzene derivatives further having one substituent group other than the acyl group, such as xanthone, 2-benzoylxanthone, xanthene, and fluorene; benzene and toluene derivatives having 3 or more different substituent groups, such as 7-acetoxy-8-methoxy-3-(2-nitrophenyl)carbostyril; aralkyl compounds such as 9-benzylacridine; and diazo compounds and azo compounds, such as 1.1'-azonaphthalene and azoxyphenol.

Illustrative examples of the naphthalene derivative include alkyl, alkenyl, and phenyl naphthalenes, such as 2-methylnaphthalene, 1-ethylnaphthalene, 2-ethylnaphthalene, and 1,2-dimethylnaphthalene; dinaphthyls such as 1,1'-dinaphthyl, 1,2'-dinaphthyl, and 2,2'-dinaphthyl; naphthylarylmethanes such as 1-benzylnaphthalene, 2-benzylnaphthalene, 1-(α,α-dichlorobenzyl)naphthalene, diphenyl-α-naphtylmethane, diphenyl-β-naphtylmethane, and di-α-naphtylmethane; napthylarylethanes such as 1,2-di-α-naphtylethane and 1,2-di-β-naphtylethane; hydronaphthalenes such as 1,2-dihydronaphthalene, 1,4-dihydronaphthalene, and 1,2,3,4-tetrahydronaphthalene; nitronaphthalenes and their derivatives, such as nitromethylnaphthalenes, nitroalkylnaphthalenes, nitrophenylnaptthalenes, halonitronaphthalenes, halodinitronaphthalenes, nitrosonaphthalenes, diaminonaphthalenes, triaminonaphthalenes, and tetraaminonaphthalenes; halogenated naphthalenes such as 1-fluoronaphthalene, 1-chloronaphthalene, and 1-chloro-3,4-dihydronaphthalene; naphthylhydroxylamines, naphthylpyrazines, and naphthylureas, such as α-naphthylhydroxylamine, β-naphthylthiohydroxylamine, N-nitroso-α-naphthylhydroxylamine, α-naphthylhydrazine, and 1,2-dibenzocarbazole; naphthalene type aralkyl compounds such as dibenzoanthracene, acenaphthene, diphenyl naphthyl chloromethane, and nitromethylnaphthalene; naphthoaldehydes and their derivatives, such as α-naphthaldehyde and 2-(2,4-dinitrophenyl)-1-(α-naphthyl)ethylene; acetonaphthenes and benzoylnaphthalenes, such as (1,2- or 5,6-)dibenzanthracene, 2'-methyl-2,1'-dinaphthyl ketone, 2-methyl-1,1'-dinaphthyl ketone, and styryl-2-naphthyl ketone; and naphthols such as 1-naphthol (α-naphthol), 2-naphthol, 1,3-dihydoxy-naphthalene, 1,5-dihydoxy-naphthalene, 1,7-dihydoxy-naphthalene, 6-hydroxy-2-naphthoic acid, 2-hydroxy-1-naphthoic acid, 1-hydroxy-2-naphthoic acid, and 1-hydroxy-8-naphthoic acid.

Illustrative examples of the polynuclear aromatic compound include: anthracene and its derivatives, such as anthracene, 1,2-dihydroanthracene, 1-chloloanthracene, 1,4-dichloroanthracene, 1-nitroanthracene, 9,10-dinitroanthracene, 1-aminoanthracene, 2-dimethylaminoanthracene, 2-anilinoanthracene, 9-methylaminoanthracene, and 1,4-diaminoanthracene; phenanthrene and its derivatives, such as phenanthrene, 9,10-dihydrophenanthrene, 1,2,3,4-tetrahydrophenanthrene, and 1-chlorophenanthrene; or polynuclear aromatic compounds and their derivatives, such as pentacene, hexacene, benzophenanthrene, benzo[a]anthracene, pyrene, and coronene.

Illustrative examples of the non-benzene type aromatic compound include azulene, cyclodecapentane, cyclotetradecaheptane, cyclooctadecanonaene, cyclotetracosadodecaene, heptalene, fulvalene, sesquifulvalene, heptafulvalene, and perinaphthene.

Among these compounds, from a viewpoint of an economic reactiveness under a mild condition and a low cost, naphthols are preferably used. Here, the aromatic compounds represented by the following general formula (1) are more preferably used, while α-naphthol is still more preferably used.

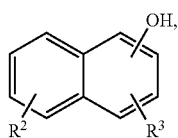

(1)

In the general formula (1), $R^2$ and $R^3$ each represent a hydrogen atom or a hydrocarbon group. Illustrative examples of the hydrocarbon group include a methyl group, an ethyl group, a n-propyl group, an isopropyl group, a n-butyl group, an isobutyl group, and a n-octyl group.

Carbonyl Compound

Any carbonyl compounds may be used without any restriction so far as they are organic compounds having a carbonyl group. Illustrative examples of the carbonyl compound include aldehydes (aldehyde compounds) such as formaldehyde, acetaldehyde, and terephthalaldehyde; ketones (ketone compounds) such as acetone, methyl ethyl ketone, and acetylacetone. These compounds may be used singly or as a combination of two or more of them. Aldehyde compounds represented by the following general formula (2) may be preferably used as the carbonyl compound.

$R^1$—CHO (2)

In the general formula (2) described above, $R^1$ represents a hydrogen atom or a hydrocarbon group (preferably hydrocarbon groups having 1 to 10 carbon atoms). Among the carbonyl compounds that are exemplified above, from industrial and economic viewpoints, formaldehyde and acetaldehyde are more preferable.

Catalyst

Illustrative examples of the catalyst include Bronsted acids such as hydrochloric acid, sulfuric acid, phosphoric acid, and citric acid; Lewis acids such as aluminum chloride, monoborane, diborane, borane trifluoride, and alumina; and bases such as ammonia, triethylamine, and alkali metal hydroxides (lithium hydroxide, sodium hydroxide, and potassium hydroxide).

Reaction Solvent

Any reaction solvents may be used without any restriction so far as they are in a liquid state at the reaction temperature and the reaction pressure. Illustrative examples of the reaction solvent include water, or organic solvents such as alcohols, ketones, and esters: for example, alcohols such as methanol, ethanol, and propanol; ketones such as acetone and methyl ethyl ketone; and esters such as methyl acetate and ethyl acetate.

The addition condensation product of the aromatic compound and the carbonyl compound is produced by causing the reaction of these reactants in the presence of the catalyst in the reaction solvent, usually in the temperature range of room temperature to 200° C. and for the period of 1 to 100 hours, while preferably in the temperature range of 30 to 150° C. and for the period of 2 to 30 hours. The aromatic compound and the carbonyl compound each may be used singly or as a combination of two or more of them.

In view of controlling the ratio of the aromatic compound dimer and the aromatic compound multimer within the range mentioned before, the addition condensation product of the aromatic compound and the carbonyl compound is produced by causing the reaction preferably in the temperature range of room temperature to 97° C. and for the period of 1 to 100 hours, while more preferably in the temperature range of 30 to 95° C. and for the period of 2 to 30 hours. The maximum reaching temperature during the reaction is preferably in the range of 60 to 97° C. It is preferable to conduct the reaction at this maximum reaching temperature for the period of 1 to 100 hours, while more preferably for the period of 2 to 30 hours.

The pH of the medium in which the condensation reaction is conducted is usually in the range of 1 to 14, while preferably in the range of 1 to 10. Here, a pH controlling agent may be used without any restriction; and from a viewpoint to properly keep the solubility of the condensation product, it is preferable to use an alkali metal hydroxide such as lithium hydroxide, sodium hydroxide, or potassium hydroxide.

The ratio of the aromatic compound to the carbonyl compound at the time of the condensation reaction may be appropriately chosen in accordance with the kind of the aromatic compound, the carbonyl compound, the reaction solvent, and the catalyst to be used, reaction time, reaction temperature, and the like. The carbonyl compound is used usually in the range of 0.1 to 10 moles, while preferably in the range of 0.5 to 3.0 moles, relative to 1 mole of the aromatic compound. The carbonyl compound is used still more preferably in the range of 0.1 to 0.999 moles, while especially preferably in the range of 0.5 to 0.99 moles, relative to 1 mole of the aromatic compound. By so doing, the ratio of the aromatic compound dimer to the aromatic compound multimer can be controlled within the range mentioned before.

By so doing, the solution containing the addition condensation product can be obtained. The addition condensation product in this solution includes the aromatic compound dimer in which two composition units derived from the aromatic compounds are bonded via one composition unit derived from the carbonyl compound and the aromatic compound multimer in which each of three or more (preferably 3 to 50) composition units derived from the aromatic compounds is bonded via one composition unit derived from the carbonyl compound; here, the ratio of the aromatic compound dimer to the aromatic compound multimer is in the range of 1:75 to 1:1,000, preferably in the range of 1:80 to 1:1,000, and more preferably in the range of 1:80 to 1:500, while still more preferably in the range of 1:80 to 1:400. The measurement method of the ratio will be described in detail in Examples.

The addition condensation compound usually includes, in addition to the aromatic compound dimer, the aromatic compound trimer (compound represented by the formula A-B-A-B-A) to the aromatic compound 50 multimer (compound represented by the formula A-B-A- . . . -B-A in which 50 of A are included).

The weight-average molecular weight of the addition condensation product of the aromatic compound and the carbonyl compound is preferably in the range of 200 to 100,000, both inclusive, while more preferably in the range of 500 to 10,000, both inclusive. Here, the weight-average molecular weight means the weight-average molecular weight in terms of the polystyrene conversion value that is measured by a gel permeation chromatography. The same is applied to the description to be followed hereinafter.

The solution including the addition condensation product after completion of the condensation reaction may be used as it is as the polymer scale adhesion preventive agent. When the solution including the addition condensation product is used as the polymer scale adhesion preventive agent, it is preferable that the addition condensation product is included in the solution with the concentration range of 0.1% to 15% by mass, both inclusive. The amount of the addition condensation product may be controlled by adding a solvent or the like.

When the solution including the addition condensation product is used as the polymer scale adhesion preventive agent, a component described below may be further added to the solution after completion of the condensation reaction.

Reducing Agent

Addition of a reducing agent brings about the following merits. Namely, the homogeneity stability of the solution of the condensation reaction product that is obtained by the condensation reaction can be improved; and a gelled product is not formed even when this solution is stored for a long period of time so that contamination of the gelled product into the polymer product can be prevented in advance thereby preventing to adversely affect the product quality. On top of these, the scale adhesion preventive effect of the scale adhesion preventive coating film that is obtained from the addition condensation product according to the present invention can be enhanced. Examples of the reducing agent include sulfite salts, phosphite salts, nitrite salts, reducing sugars, and thiourea dioxide.

Illustrative examples of the sulfite salt include ammonium sulfite, potassium sulfite, sodium sulfite, ammonium hydrogen sulfite, sodium hydrogen sulfite, sodium dithionite ($Na_2S_2O_4$), and rongalite.

Illustrative examples of the phosphite salt include ammonium phosphite, sodium phosphite, potassium phosphite, calcium phosphite, uranyl phosphite, cobalt phosphite, ferrous phosphite, ferric phosphite, copper phosphite, barium phosphite, hydrazinium phosphite, ammonium hydrogen phosphite, sodium hydrogen phosphite, potassium hydrogen phosphite, calcium hydrogen phosphite, cobalt hydrogen phosphite, cuprous hydrogen phosphite, cupric hydrogen phosphite, ferrous hydrogen phosphite, ferric hydrogen phosphite, lead hydrogen phosphite, barium hydrogen phosphite, magnesium hydrogen phosphite, manganese hydrogen phosphite, and hydrazinium hydrogen phosphite.

Illustrative examples of the nitrite salt include ammonium nitrite, sodium nitrite, potassium nitrite, calcium nitrite, zinc nitrite, silver nitrite, cobalt potassium nitrite, cobalt sodium nitrite, strontium nitrite, cesium nitrite, cerium nitrite, cupric nitrite, nickel nitrite, barium nitrite, magnesium nitrite, lithium nitrite, and rubidium nitrite.

Reducing sugars are sugars that have a free aldehyde group or carbonyl group and exhibit a reducing property. Illustrative examples thereof include maltose, lactose, and grape sugar (glucose).

These reducing agents may be used singly or as a combination of two or more of them. Among those reducing agents exemplified above, sulfite salts and thiourea dioxide are preferable.

In the condensation reaction, the reducing agent can be added into the reaction system or into the solution of the addition condensation product at least in one stage among prior to initiation of the condensation reaction, during the condensation reaction, and after completion of the condensation reaction. In the present invention, however, in the stage prior to initiation of the condensation reaction, it is preferable not to add to the reaction system the reducing agent of 0.05 or more mole equivalent to the aromatic compound, which is added prior to initiation of the condensation reaction. By so doing, the ratio can be controlled within the range described above.

In the above paragraph, the expression "prior to initiation of the condensation reaction" means the stage after preparation of the solution of both the reaction raw materials and the like but prior to completion of the process of raising the temperature of the reaction system from room temperature to a prescribed reaction temperature, specifically, the stage prior to completion of the process of raising the temperature of the reaction system from room temperature to 50° C. The expression "during the condensation reaction" means the stage after the temperature of the reaction system reached the prescribed reaction temperature but prior to completion of the condensation reaction so that the unreacted reaction raw materials still remain in the reaction system. The expression "after completion of the condensation reaction" means the stage after completion of the condensation reaction so that the addition condensation product exists in the state of solution. It is presumed that the addition reaction of the carbonyl compound to the aromatic compound progresses rapidly at the temperature of 50° C. or higher.

When the reducing agent is used, the use amount thereof is usually in the range of 0.01 to 10 parts by mass, while preferably in the range of about 0.1 to about 3 parts by mass, relative to 100 parts by mass of the addition condensation product.

Water-Soluble Polymer

In order to enhance the hydrophilicity of the coating film thereby improving the scale adhesion preventive property thereof, a water-soluble polymer may be added to the solution of the addition condensation product of the aromatic compound and the carbonyl compound. Illustrative examples of the water-soluble polymer include an anionic polymer compound, an amphoteric polymer compound, a cationic polymer compound, a nonionic polymer compound, and a polymer compound having a hydroxy group. In the case that the water-soluble polymer is added, the K value of the water-soluble polymer is preferably within the range where the performance to enhance the hydrophilicity of the coating film is sufficiently well and where there is no problem in the solubility thereof into a solvent. Specifically, the K-value of the water-soluble polymer [K-value based on the Fikentscher equation (25° C.)] is preferably in the range of 10 to 200, both inclusive, while more preferably in the range of 80 to 150, both inclusive. Preferably, the content of the water-soluble polymer is set within the range in which there is no handling problem caused by increase of the solution viscosity. Specifically, the content of the water-soluble polymer is preferably in the range of 0.001 to 50% by mass, both inclusive, while more preferably in the range of 0.01 to 30% by mass, both inclusive.

pH-Controlling Agent

The pH of the solution of the addition condensation product of the aromatic compound and the carbonyl compound may be appropriately chosen in accordance with the kind of the compounds to be used. When pH control is necessary, an acidic and an alkali compound may be appropriately used as the pH-controlling agent. Illustrative examples of the acidic compound include hydrochloric acid, sulfuric acid, nitric acid, phosphoric acid, diphosphoric acid, and myo-inositol-1,2,3,4,5,6-hexaphosphoric acid. Illustrative examples of the alkali compound include: alkali metal compounds such as LiOH, NaOH, KOH, $Na_2CO_3$, and $Na_2HPO_4$; and amine type compounds such as $NH_3$, methylamine, ethylamine, and ethylenediamine. When pH control is carried out, pH is preferably in the range of 6 to 14, while more preferably in the range of 8 to 13.

In the solution of the addition condensation product of the aromatic compound and the carbonyl compound that is used in the present invention, a component other than the components described above may be added thereinto as needed so far as the object and advantageous effects of the present invention are not impaired. Here, the addition amount thereof in the solution is preferably in the range of 0 to 50% by mass, both inclusive. Specific examples thereof include an inorganic colloid, an alkali metal silicate salt, and an antioxidant.

Polymerization Vessel and Polymer Production Method

The polymerization vessel is the polymerization vessel that is used for polymerization of a monomer and the addition condensation product adheres to the inner wall surface of the vessel to which the monomer contacts. The solution containing the addition condensation product is usually applied onto the inner wall surface of the polymerization vessel to adhere the addition condensation product thereto as a coating film. Here, there is no particular restriction as to the volume of the polymerization vessel.

In one example, a schematic diagram of the apparatus to apply the solution of the addition condensation product of the aromatic compound and the carbonyl compound according to the present invention is illustrated in FIG. 1. With reference to FIG. 1, the process for applying the solution of the addition condensation product of the aromatic compound and the carbonyl compound according to the present invention will be described.

Although there is no particular restriction as to the method for applying the solution of the addition condensation product of the aromatic compound and the carbonyl compound according to the present invention, it is preferable that the above-mentioned coating solution is applied through a nozzle by using, for example, nitrogen, air, or steam as a carrier to the surfaces of a metal plate, the inner wall surface of the polymerization vessel, and the like. There is no particular restriction either as to the material of the substrate, namely, the metal plate and the inner wall surface of the polymerization vessel. Illustrative examples the usable material include a carbon steel, a stainless steel, a nickel alloy, a titanium alloy, and an aluminum alloy. Especially from a viewpoint to satisfy both the anti-corrosion property and the economic rationality, a stainless steel is preferably used. The surfaces of the metal plate and inner wall of the polymerization vessel may be polished mechanically or electrolytically, or plated as needed.

Examples of the coating method to apply the solution of the addition condensation product of the aromatic compound and the carbonyl compound according to the present invention to the surface of the polymerization vessel include the coating process described below.

Coating Process

Preheating of Inner Wall Surface and the Like of the Polymerization Vessel with Steam With referring to FIG. 1, hot water or the like is passed through a jacket 2 that is attached to a polymerization vessel 1 to preheat the inner wall surface of the polymerization vessel to a temperature of 20° C. or more, while preferably in the temperature range of 30 to 95° C. The upper section of the polymerization vessel 1 is provided with a coating nozzle 3 directing downward. To the coating nozzle 3 is connected a line 4 through which the steam and the coating liquid are supplied from the outside of the polymerization vessel 1. To the line 4 are connected a steam supplying line 5, a first coating liquid supplying line 6, and a second coating liquid supplying line 7, via a valve V1, a valve V2, and a valve V3, respectively. As necessary, from the coating nozzle 3, a steam (steam or super-heated steam) is blown into the polymerization vessel 1 to also preheat a baffle, stirring blades, and the like (not illustrated in the FIGURE).

In this equipment, the steam is supplied to the coating nozzle 3 through a flow meter 9, the line 5, and the line 4 from a steam supplier 8.

First Step Application

The steam is supplied to the coating nozzle 3, and the first coating liquid containing the solution of the addition condensation product of the aromatic compound and the carbonyl compound and stored in a first coating liquid tank 10 is supplied to the coating nozzle 3 through the lines 6 and 4 by means of a pump 11 or an aspirator valve (not illustrated in the FIGURE). Here, the alphabet "P" in the FIGURE represents a pressure gauge. The first coating liquid containing the solution of the addition condensation product of the aromatic compound and the carbonyl compound is carried with the steam and applied onto the inner wall surface of the polymerization vessel 1, the baffle surface, the stirring blade surface, and the like, to which the monomer contacts during polymerization, thereby forming a first coating layer. The mixing ratio of the steam (G) to the coating liquid (L), i.e., (L/G), is preferably in the range of 0.01 to 1.0, while more preferably in the range of 0.02 to 0.3, in terms of the flow amount ratio on the mass basis.

(Second Step Application: This can be Omitted as Necessary)

Subsequently, a second coating liquid containing an auxiliary agent and stored in a second coating liquid tank 12 is supplied under the running state of the steam to the coating nozzle 3 via the lines 7 and 4 by means of a pump 13 so as to be applied onto the first coating layer to form a second coating layer (not especially illustrated in the FIGURE). Similarly to the first step application, in this second step application, too, the second coating layer is formed simultaneously with application. In this second step application, too, the mixing ratio of the steam (G) to the coating liquid (L), i.e., (L/G), is preferably in the range of 0.01 to 1.0, while more preferably in the range of 0.02 to 0.3, in terms of the flow amount ratio on the mass basis.

In the second step application, the compositions of the first coating liquid and the second coating liquid may be the same, or different, so far as the compositions of these liquids are within the before-mentioned range. Here, it is preferable that the addition condensation product is included in the first coating liquid or the second coating liquid, or in both the first coating liquid and the second coating liquid.

Water Washing

After stopping the supply of the steam and the coating liquid, the inside of the polymerization vessel 1 is cleaned with washing water that is stored in a water tank 14. Upon opening V4, the washing water is supplied to the inside of the polymerization vessel 1 from a nozzle 17 via a line 16 by means of a pump 15. In the case that the effect to the product quality is small, the water washing may be unnecessary.

Auxiliary Agent

In the coating method described above, an auxiliary agent may be added to the second coating liquid as necessary so far as the object and the advantageous effects of the present invention are not impaired. Preferably, the addition amount thereof in this liquid is in the range of 0 to 50% by mass, both inclusive. Specifically, examples thereof include: water-soluble polymers such as polyvinyl alcohol, partially saponified polyvinyl acetate, poly-N-vinyl pyrrolidone, and hydroxypropyl methylcellulose; acids such as hydrochloric acid, sulfuric acid, nitric acid, phosphoric acid, diphosphoric acid, o-inositol-1,2,3,4,5,6-hexaphosphoric acid, and citric acid; salts of acidic substances such as sodium dihydrogen phosphate, disodium hydrogen phosphate, triammonium phosphate, calcium hydrogen phosphate, disodium dihydrogen diphosphate, and calcium dihydrogen diphosphate; bases such ammonia, triethylamine, and ethylenediamine; and inorganic colloids such as colloidal silica.

In the same way as the coating method as described above, the solution of the addition condensation product of the aromatic compound and the carbonyl compound may be applied to form a coating into the inner wall surface of the polymerization vessel 1 by using the steam as a career. In this case, the steam that is used as the career may be any of a usual steam and a superheated steam; especially the steam with the pressure in the range of 0.1 to 3.5 MPaG is preferable, while more preferably in the range of 0.28 to 2.0 MPaG. The temperature of the steam is preferably in the range of 120 to 270° C., while more preferably in the range of 140 to 230° C. The pressure and temperature of the steam are the values measured before the steam and the coating liquid are mixed, for example, the values measured in the steam supplying line 5 in FIG. 1. The coating application period of the solution of the addition condensation product of the aromatic compound and the carbonyl compound is preferably within the range in which the sufficiently effective coating film can be formed and yet economically feasible; thus specifically, the period is preferably in the range of 1 to 600 seconds, both inclusive, while more preferably in the range of 10 to 300 seconds, both inclusive.

The polymerization vessel that is going to be coated is applied with the solution of the addition condensation product of the aromatic compound and the carbonyl compound to the inner wall surface thereof to which the monomer contacts during the polymerization reaction. Here, the inner volume of the vessel is preferably 1 m$^3$ or more; especially in view of productivity, the inner volume is preferably in the range of 10 to 600 m$^3$. The polymerization vessel may be equipped with one, or a combination of two or more equipment selected from a jacket, a coil, a baffle, a reflux condenser with which the monomer can be condensed during the polymerization reaction, and an inner jacket. It is preferable that the polymerization vessel is equipped at least with a reflux condenser with which the monomer can be condensed during the polymerization reaction because with this the inside of the polymerization vessel can be efficiently cooled.

The solution of the addition condensation product of the aromatic compound and the carbonyl compound according to the present invention is applied to the inside of the polymerization vessel at the process in which an olefinic polymer is produced; especially, the solution is preferably used at the process in which a monomer having an ethylenic double bond is polymerized. Examples of the monomer having an ethylenic double bond include: halogenated vinyls such as vinyl chloride; halogenated vinylidenes such as vinylidene chloride; vinyl esters such as vinyl acetate and vinyl propionate; esters or salts of acrylic acid and methacrylic acid; esters or acid anhydrides of maleic acid and fumaric acid; diene type monomers such as butadiene, chloroprene, and isoprene; styrene; acrylonitrile; and vinyl ethers. In particular, the solution of the addition condensation of the aromatic compound and the carbonyl compound to be applied in the polymerization vessel can be preferably used at the process in which a vinyl halide such as vinyl chloride, a vinylidene halide such as vinylidene chloride, or a monomer mixture containing one of these monomers as the major component and also containing another monomer, is subjected to suspension polymerization or emulsion polymerization in an aqueous medium, thereby producing a polymer or copolymer of the monomer(s) having an ethylenic double bond, or a copolymer of the monomer mixture.

The solution of the addition condensation product of the aromatic compound and the carbonyl compound according to the present invention exhibits high durability even when used in polymerization of monomers such as α-methylstyrene, acrylate esters, methacrylate esters, acrylonitrile, and vinyl acetate that have a high solubility of a coating film formed by a heretofore known polymer scale adhesion preventive agent. Thus, this solution can be preferably used even for production of polymer beads or a latex of polystyrene, poly(methyl methacrylate), polyacrylonitrile, or the like, and for production of synthetic rubbers such as a styrene butadiene rubber (SBR), an acrylonitrile butadiene rubber (NBR), a chloroprene rubber (CR), an isoprene rubber (IR), and a butyl rubber (IIR) (these synthetic rubbers are usually produced by emulsion polymerization), and for production of an ABS resin.

In polymerization of one, or two or more of these monomers, the object and effect of prevention of the polymer scale can be achieved regardless of the polymerization method such as suspension polymerization, emulsion polymerization, bulk polymerization, and solution polymerization, or even when the polymerization is conducted in the presence of any additive such as an emulsifier, a stabilizer, a lubricant, a plasticizer, a pH-controlling agent, or a chain-transfer agent. For example, in suspension polymerization or emulsion polymerization of a vinyl type monomer, various additives may be added to the polymerization system as needed. Illustrative examples of the additive like this include suspension stabilizers such as partially saponified polyvinyl alcohol and methyl cellulose; anionic emulsifiers such as sodium lauryl sulfate; nonionic emulsifiers such as sorbitan monolaurate and polyoxyethylene alkyl ether; stabilizers such as lead tribasic sulfate, calcium stearate, dibutyltin dilaurate, and dioctyltin mercaptide; chain-transfer agents such as trichloroethylene and mercaptans; and various pH-controlling agents. Even when these additives are present in the polymerization system, adhesion of the polymer scale can be effectively prevented.

The solution of the addition condensation product of the aromatic compound and the carbonyl compound according to the present invention can exhibit the intended polymer scale adhesion preventive effect, even when any polymerization initiator is used, without being affected by the type of the polymerization initiator. Illustrative examples of the polymerization initiator include t-butylperoxy neodecanoate, bis(2-ethylhexyl)peroxy dicarbonate, 3,5,5-trimethylhexanoyl peroxide, α-cumylperoxy neodecanoate, cumene hydroperoxide, cyclohexanone peroxide, t-butylperoxy pivalate, bis(2-ethoxyethyl)peroxy dicarbonate, dibenzoyl peroxide, diisopropylbenzene hydroperoxide, lauroyl peroxide, 2,4-dichlorobenzoyl peroxide, diisopropylperoxy dicarbonate, α,α'-azobisisobutylonitrile, α,α'-azobis-2,4-dimethyl valeronitrile, di-2-ethylhexyldiperoxy isophthalate, potassium persulfate, and ammonium persulfate.

Other conditions upon polymerizing various monomers by using the polymerization initiators mentioned above may be the same as those used conventionally; so, there is no particular restriction so far as the advantageous effects of the present invention are not impaired. Specifically, although typical polymerization conditions will be described below with referring to the cases of suspension polymerization, solution polymerization, and bulk polymerization, as the examples of polymerization of various monomers by using the polymerization initiators mentioned above, the present invention is not restricted by these polymerization conditions and the like.

In the case of suspension polymerization, first water and a dispersant are charged into the polymerization vessel, followed by charging of a polymerization initiator thereinto. Next, the inside of the polymerization vessel is either evacuated to the pressure range of about 0.001 to 101 kPa·G (about 0.01 to 760 mmHg) or set at an atmospheric pressure. Then, the monomer is charged thereinto with the amount thereof enough for raising the inner pressure of the polymerization vessel usually in the range of 49 to 2,940 kPa·G (0.5 to 30 kgf/cm$^2$·G); and then, the polymerization is conducted in the reaction temperature range of 30 to 150° C. During polymerization, one, or two or more of water, the dispersant, and the polymerization initiator may be added as needed. The reaction temperature during polymerization varies depending on the monomer to be polymerized; for example, in the case of vinyl chloride the polymerization is carried out in the temperature range of 30 to 80° C., and in the case of styrene the polymerization is conducted in the temperature range of 50 to 150° C. The polymerization is deemed to have completed either when the inner pressure of the polymerization vessel has dropped to the value in the range of 0 to 686 kPa·G (0 to 7 kgf/cm$^2$·G) or when the difference between the inlet temperature and the outlet temperature of the cooling water flowing in and out of the cooling jacket fitted to around outside of the polymerization vessel has become substantially nil (namely, when heat generation due to the polymerization reaction has been subsided). The amounts of water, the dispersant, and the initiator that are charged for the polymerization are usually in the range of 20 to 500 parts by mass for water, in the range of 0.01 to 30 parts by mass for the dispersant, and in the range of 0.01 to 5 parts by mass for the polymerization initiator, relative to 100 parts by mass of the monomer.

In the case of solution polymerization, an organic solvent such as toluene, xylene, or pyridine is used in place of water as the polymerization medium. A dispersant may be used as needed. In general, other polymerization conditions are the same as those of the suspension polymerization described above.

In the case of bulk polymerization, the inside of the polymerization vessel is either evacuated to the pressure of about 0.001 to 101 kPa·G (in the range of about 0.01 to 760 mmHg) or set at an atmospheric pressure. Then, the monomer and a polymerization initiator are charged into the polymerization vessel; and then, the polymerization is conducted at the reaction temperature of −10 to 250° C. For example, in the case of vinyl chloride the polymerization can be conducted in the temperature range of 30 to 80° C., and in the case of styrene, the polymerization can be conducted in the temperature range of 50 to 150° C.

The present invention shall not be restricted by the embodiments described above. The compositions that are arbitrary combination of the composition elements described above shall be included in the present invention. Further effects and modification examples may be readily obtained by a person ordinarily skilled in the art. Therefore, wider embodiments of the present invention are not limited to the embodiments described above; thus, they may be variously modified.

EXAMPLES

Hereinafter, although on the basis of Examples, the present invention will be described specifically, the present invention is not limited to these Examples.

Synthesis Example 1

The reactor having been fully displaced with a nitrogen gas by flowing the nitrogen gas therethrough was charged with 615 mL of deionized water; then with stirring, the content in the reactor was preheated to the temperature of 35° C., followed by addition of 24.2 g of sodium hydroxide and 112.5 g of α-naphthol, and furthermore, 60 g of an aqueous solution of 37% by weight of formaldehyde. After the resulting mixture was stirred for 30 minutes, the temperature of the inside of the reactor was raised to 78° C.; then, the mixture in the reactor was caused to react for 3 hours, and then, this was cooled to 40° C. To this were further added 815 mL of deionized water, 200 g of N-methylpyrrolidone, and 15 g of sodium dithionite to obtain a solution of the condensation product No. 1.

To this solution of the condensation product No. 1 was added a mixed solution of 4.45 g of sodium hydroxide, 13.3 g of an aqueous solution of 50% by weight of myo-inositol-1,2,3,4,5,6-hexaphosphoric acid, and 155 mL of deionized water; and then, the resulting mixture was stirred for 90 minutes to obtain the coating liquid No. 11. The ratio of the aromatic compound dimer to the aromatic compound multimer was 1:341, the pH thereof was 12.6, and Mw was 1,900.

Synthesis Example 2

The condensation product No. 2 and the coating liquid No. 12 were obtained in the same way as Synthesis Example 1 except that 15 g of sodium dithionite was not added all at once after completion of the reaction, but 1.5 g thereof was added prior to the addition of α-naphthol and 13.5 g thereof was added during the reaction (for 1.5 hours after the temperature was raised to 78° C.). The ratio of the aromatic compound dimer to the aromatic compound multimer was 1:133, the pH thereof was 12.5, and Mw was 1,600.

Here, note that in Synthesis Example 2, the reducing agent, the amount of which was equal to or more than 0.05 mole equivalent relative to the aromatic compound which was added prior to initiation of the condensation reaction, was not added to the reaction system prior to initiation of the condensation reaction.

Synthesis Example 3

The condensation product No. 3 and the coating liquid No. 13 were obtained in the same way as Synthesis Example 1 except that 15 g of sodium dithionite was not added all at once after completion of the reaction but 1.5 g thereof was added prior to addition of α-naphthol and 13.5 g thereof was added after completion of the reaction. The ratio of the aromatic compound dimer to the aromatic compound multimer was 1:199, the pH thereof was 12.2, and Mw was 1,900.

Here, note that in Synthesis Example 3, the reducing agent, the amount of which was equal to or more than 0.05 mole equivalent relative to the aromatic compound which was added prior to initiation of the condensation reaction, was not added to the reaction system prior to initiation of the condensation reaction.

Synthesis Example 4

The condensation product No. 4 and the coating liquid No. 14 were obtained in the same way as Synthesis Example 1 except that 15 g of sodium dithionite was not added after completion of the reaction but this was added prior to addition of α-naphthol. The ratio of the aromatic compound dimer to the aromatic compound multimer was 1:52, the pH thereof was 12.4, and Mw was 1,300.

Synthesis Example 5

To the reactor were charged 930 mL of deionized water and 50 mL of ethanol, and with stirring, 10 g of poly(N-vinyl-2-pyrrolidone) having the weight-average molecular weight of 2,800,000. After dissolution of poly(N-vinyl-2-pyrrolidone) was visually confirmed, an aqueous solution of calcium dihydrogen diphosphate (solution obtained by dissolving 500 mg of calcium dihydrogen diphosphate in 20 mL of deionized water) was added thereinto; then, the resulting mixture was stirred for 5 hours to obtain the coating liquid No. 21.

Comparative Example 1

The reactor having been fully displaced with a nitrogen gas by flowing the nitrogen gas therethrough was charged with 36.0 kg (250 moles) of 1-naphthol and 180 L of an aqueous 1N NaOH solution (7.2 kg (180 moles) of NaOH), followed by raising the temperature thereof to 70° C. with stirring. Then, this reaction mixture was charged dropwise with 19.75 kg of an aqueous solution of formaldehyde (containing 1.92% by weight of formaldehyde) at a constant rate during 1.5 hours. During the period until completion of the dripping, the inside of the reactor was kept at the temperature not more than 80° C. Next, the reaction mixture was continuously stirred for 3 hours, during which period the temperature thereof was lowered to 60° C. Then, the temperature of the reaction mixture was raised to 98° C.; and the reaction was conducted at 98° C. for 1.5 hours. Next, the reaction mixture was cooled to obtain the condensation product No. 5.

This solution of the condensation product No. 5 was charged with a mixed solution of 4.45 g of sodium hydroxide, 13.3 g of an aqueous solution of 50% by weight of myo-inositol-1,2,3,4,5,6-hexaphosphoric acid, and 155 mL of deionized water; and then, the resulting mixture was stirred for 90 minutes to obtain the coating liquid No. 15. The ratio of the aromatic compound dimer to the aromatic compound multimer was 1:1.

Comparative Example 2

The reactor having been fully displaced with a nitrogen gas by flowing the nitrogen gas therethrough was charged with 1 L of deionized water, 180 g of 1-naphthol, and 38 g of sodium hydroxide as a catalyst; then, the resulting mixture was warmed to 70° C. in an oil bath, which was then followed by gradual addition of 102 g of an aqueous 37% formaldehyde solution dropwise under the flow of a nitrogen gas. After completion of the dripping, this solution was mixed with 400 g of an aqueous 12% sodium isoascorbate solution. The reaction mixture was cooled to 60° C., at which temperature the reaction was conducted for 3 hours, then, the temperature thereof was raised to 98° C., at which temperature the reaction was further conducted for 1.5 hours to obtain the condensation product No. 6.

Next, water was added into the reaction mixture to bring the solid concentration therein to 5% to obtain the coating liquid No. 16. The ratio of the aromatic compound dimer to the aromatic compound multimer was 1:34,000.

Application

Steam One-Step Application

A polymerization reactor made of a stainless steel with the inner volume of 2 m³ was used as the polymerization vessel 1. The inner wall surface of the polymerization vessel 1 is preheated to 45° C. by flowing the hot water through the jacket 2. The valve V1 is opened to blow a steam of 0.717 MPaG (171.4° C.) into the polymerization vessel with a flow rate of 240 kg/hour for 60 seconds to preheat the inside of the vessel; then, the valve V2 is opened to apply the first coating liquid containing the solution of the addition condensation product of the aromatic compound and the carbonyl compound described in Table 1 at the flow rate of 120 mL/minute for 120 seconds by using the above-mentioned steam as a career. Then, the valves V1 and V2 are closed. Charge of the hot water into the jacket 2 is halted.

Steam Two-Step Application

A polymerization reactor made of a stainless steel with the inner volume of 2 m³ was used as the polymerization vessel 1. The inner wall surface of the polymerization vessel 1 is preheated to 45° C. by flowing the hot water through the jacket 2. The valve V1 is opened to blow a steam of 0.717 MPaG (171.4° C.) into the polymerization vessel with a flow rate of 240 kg/hour for 60 seconds to preheat the inside of the vessel; then, the valve V2 is opened to apply the first coating liquid (for undercoating) containing the solution of the addition condensation product of the aromatic compound and the carbonyl compound described in Table 1 at the flow rate of 120 g/minute for 120 seconds by using the above-mentioned steam as a career to form the first layer. Then, the valve V2 is closed. Next, the valve V3 is opened to apply the second coating liquid (for overcoating) containing the auxiliary agent described in Table 1 at the flow rate of 285 g/minute for 40 seconds by using the above-mentioned steam as a career to form the second layer onto the first layer. Then, the valves V1 and V3 are closed. Charge of the hot water into the jacket 2 is halted.

Polymerization

The polymerization vessel having been treated with the above-described "Application" was charged with 200 parts by weight of deionized water, 0.020 part by weight of a partially saponified polyvinyl alcohol, and 0.026 part by weight of 2-hydroxypropyl methylcellulose [tradename: Metolose, manufactured by Shin-Etsu Chemical Co., Ltd., degree of methoxyl group substitution (average number of the hydroxy group in the cellulose glucose ring unit displaced with the methoxyl group): 1.9, degree of 2-hydroxypropyl group substitution (mole number of the hydroxyalkoxyl group added to the cellulose glucose ring unit): 0.25]; then, the inside of the polymerization vessel was degassed until 50 mmHg. Next, 100 parts by weight of vinyl chloride monomer (VCM) was charged, and then, with stirring the reaction mixture in the polymerization vessel, 0.03 part by weight of t-butylperoxy neodecanoate was charged by pressure filling with a pump. Then, the temperature of the inside of the polymerization vessel was raised to 52° C. by flowing the hot water through the jacket. Then, the polymerization was conducted with keeping the temperature of the inside of the polymerization vessel at 52° C. by flowing the cooling water through the jacket.

With stirring the charged raw material, the temperature of the inside of the vessel was raised by flowing the hot water through the jacket 2, and when the temperature reached 52°

C., the polymerization was conducted with keeping the temperature of the inside of the polymerization vessel at 52° C. by flowing the cooling water through the jacket 2. The polymerization was terminated when the pressure of the inside of the vessel reduced to 5 kgf/cm²·G (0.49 MPa·G). After the unreacted monomer was recovered, the slurry of the reaction mixture was withdrawn from the polymerization vessel, dehydrated and dried to obtain a vinyl chloride polymer.

Measurement of Composition of the Addition Condensation Product of Aromatic Compound and Carbonyl Compound The composition of the addition condensation product of the aromatic compound and the carbonyl compound was measured by a high-performance liquid chromatography (HPLC) with the condition described below.
Instrument Used:
Liquid chromatography instrument: general-purpose HPLC Prominence, manufactured by Shimadzu Corp.
   System controller: CBM-20A
   Liquid supply unit: LC-20AD (2 units)
   Online degassing apparatus: DGU-20A3
   Auto-sampler: SIL-20ACHT
   Column oven: CTO-20A
   UV-VIS detector: SPD-20A
   Column:
   (1) Guard column: Waters Puresil™ C18 Guard Column, 100 Å, 5 μm, 3.9 mm×20 mm (one column)
   (2) Analysis column: Waters HPLC COLUMNS, μ-Bondasphere DeltaPak C18 Column, 100 Å, 5 μm, 3.9 mm×150 mm (one column)
   Eluting solution A: 2 mL of acetic acid in 1 L of distilled water
   Eluting solution B: 1 mL acetic acid in 1 L of acetonitrile
   Flow rate of eluting solution A+eluting solution B: 1.0 mL/min
   Gradient condition of eluting solution: first, the ratio of the eluting solution B to the total eluting solution was linearly changed from 40% by volume to 100% by volume in concentration spending 30 minutes. Next, the ratio of the eluting solution B to the total eluting solution was kept at 100% by volume for 10 minutes.
   Column oven temperature: 40° C.
   Detection wavelength: 288 nm
   Sample injection volume: 20 μL
   Sample Preparation: Acetonitrile was measured to be 10.0 mL, and mixed with 20 μL of 0.5 N hydrochloric acid. Next, 20 μL of the solution of the addition condensation product of the aromatic compound and the carbonyl compound was added to this acetonitrile solution with stirring, and sufficiently mixed. The resulting specimen was filtrated through a filter made of polytetrafluoroethylene and having a pore diameter of 0.45 μm; then the filtrate was immediately measured.
   Peak Retention Time (in the case that the aromatic compound is 1-naphthol and the carbonyl compound is formaldehyde):
   Aromatic compound dimer formed by reaction of the aromatic compound and the carbonyl compound with the mole ratio of 2:1 (3 isomers): 12.3 minutes, 12.7 minutes, undetectable
   Trimer or higher of the aromatic compound multimer: all peaks in the retention time of 13 to 40 minutes
   Ratio of the aromatic compound dimer to the aromatic compound multimer: 1:(total peak area between 13 to 40 minutes)/(peak area at 12.3 minutes+peak area at 12.7 minutes)

Measurement of Weight-average Molecular Weight of Addition Condensation Product of Aromatic Compound and Carbonyl Compound The weight-average molecular weight of the addition condensation product of the aromatic compound and the carbonyl compound was measured by a high-performance liquid chromatography (HPLC) with the following condition.
Instrument Used:
Liquid chromatography instrument: General-purpose HPLC Prominence, manufactured by Shimadzu Corp.)
   System controller: CBM-20A
   Liquid supply unit: LC-20AD
   Online degassing apparatus: DGU-20A3
   Auto-sampler: SIL-20ACHT
   Column oven: CTO-20A
   UV-VIS detector: SPD-20A
   Column:
   (1) Guard column: Phenogel Linear/Mixed, 5 μm, 4.6 mm×30 mm (one column)
   (2) Analysis column: Phenogel 5 μm, 50 Å, 4.6 mm×300 mm (one column);
   Phenogel 5 μm, 1,000 Å, 4.6 mm×300 mm (one column)
   Eluting solution: tetrahydrofuran (without stabilizer)
   Flow rate of eluting solution: 1.0 mL/min
   Column oven temperature: 60° C.
   Detection wavelength: 290 nm
   Sample injection volume: 10 μL
   Standard polystyrene: Mp=1.20×10³, 2.94×10³, 6.18×10³, 1.26×10⁴, 1.65×10⁴, and 5.51×10⁴ (6 standards)
   Sample Preparation:
   Tetrahydrofuran was measured to be 10.0 mL, and mixed with 20 μL of 0.5N hydrochloric acid. Next, 20 μL of the solution of the addition condensation product of the aromatic compound and the carbonyl compound was added to this tetrahydrofuran solution with stirring, and sufficiently mixed. The resulting specimen was filtrated through a filter made of polytetrafluoroethylene and having a pore diameter of 0.45 μm; then the filtrate was immediately measured.
   Peak Retention Time (in the case that the aromatic compound is 1-naphthol and the carbonyl compound is formaldehyde):
   1-Naphthol: 7.2 minutes
   Dimer or higher of the aromatic compound multimer: all peaks before 7.0 minutes
   The weight-average molecular weight (Mw) in terms of the standard polystyrene conversion value was calculated from the all peaks eluted before 7.0 minutes.
   Accumulability
   This was evaluated in accordance with the following standards.
   ⊚: There is no decrease in the overall heat transfer coefficient of the jacket of the polymerization vessel due to accumulation of the NS agent; so, cleaning of the inside of the vessel is not necessary over 1 year.
   ○: There is a decrease in the overall heat transfer coefficient of the jacket of the polymerization vessel due to accumulation of the NS agent, resulting in the decrease thereof of 30% or more within the time range of more than 6 months and 1 year or less; so, cleaning of the inside of the vessel is necessary.
   x: There is a significant decrease in the overall heat transfer coefficient of the jacket of the polymerization vessel due to accumulation of the NS agent, resulting in the decrease thereof of 30% or more within 6 months; so, the cleaning of the inside of the vessel is necessary.

Here, the overall heat transfer coefficient of the jacket of the polymerization vessel was calculated from the following formulae.

$$U = \frac{(To - Ti) \times (F \times 1000) \times 1.0}{A \times \Delta Tln} \quad (1)$$

$$\Delta Tln = \frac{(To - Ti)}{\ln\left(\frac{T - Ti}{T - To}\right)}$$

U: Overall heat transfer coefficient of the jacket of the polymerization vessel [kcal/m$^2$·h·° C.]

Ti: Temperature of the cooling water at the inlet to the jacket of the polymerization vessel (° C.)

To: Temperature of the cooling water at the outlet of the jacket of the polymerization vessel (° C.)

T: Polymerization temperature in the polymerization vessel (° C.)

F: Flow rate of the cooling water in the jacket of the polymerization vessel (m$^3$/hour)

A: Heat transfer area of the jacket of the polymerization vessel (m$^2$)

Evaluation results of accumulability are summarized in Table 1.

TABLE 1

|  | First application liquid | Second application liquid | Accumulability |
|---|---|---|---|
| One-step application | Coating liquid No. 11 | — | ⊚ |
| Two-step application | Coating liquid No. 11 | Coating liquid No. 21 | ⊚ |
| One-step application | Coating liquid No. 12 | — | ⊚ |
| Two-step application | Coating liquid No. 12 | Coating liquid No. 21 | ⊚ |
| One-step application | Coating liquid No. 13 | — | ⊚ |
| Two-step application | Coating liquid No. 13 | Coating liquid No. 21 | ⊚ |
| One-step application | Coating liquid No. 14 | — | X |
| Two-step application | Coating liquid No. 14 | Coating liquid No. 21 | X |
| One-step application | Coating liquid No. 15 | — | X |
| Two-step application | Coating liquid No. 15 | Coating liquid No. 21 | X |
| One-step application | Coating liquid No. 16 | — | X |
| Two-step application | Coating liquid No. 16 | Coating liquid No. 21 | X |

Among these results, when the coating liquid No. 11 was used, cleaning of the inside of the vessel was not necessary over 3 years regardless of the one-step application and the two-step application; when the coating liquid No. 13 was used, cleaning of the inside of the vessel was not necessary over 2 years regardless of the one-step step application and the two-step application.

When the synthesis was done with the methods of Synthesis Examples 1, 2, and 3, the same effects as the coating liquids No. 11, No. 12, and No. 13 could be recognized so far as the ratio of the aromatic compound to the carbonyl compound in the condensation reaction or the reaction temperature thereof (maximum reaching temperature) was within the before-mentioned preferable range, even if the ratio or the temperature was not the same as those of the above Examples.

With the addition condensation product according to the present embodiment, a coating film capable of realizing prevention of a polymer scale from adhering to an inner wall surface and the like of a polymerization vessel can be formed as the polymer scale adhesion preventive agent onto the inner wall surface of the polymerization vessel for production of a polymer of a monomer having an ethylenic double bond; so, a productivity of the polymer can be improved.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An addition condensation product of an aromatic compound and a carbonyl compound, the addition condensation product comprising:
   an aromatic compound dimer in which two composition units derived from the aromatic compounds are bonded via one composition unit derived from the carbonyl compound; and
   an aromatic compound multimer in which each of three or more composition units derived from the aromatic compounds is bonded via one composition unit derived from the carbonyl compound, wherein
   a ratio of the aromatic compound dimer to the aromatic compound multimer is in a range of 1:75 to 1:1,000, and
   the addition condensation product is a reaction product of the carbonyl compound in a range of 0.1 to 0.999 moles relative to 1 mole of the aromatic compound.

2. The addition condensation product according to claim 1, wherein the aromatic compound is a naphthol.

3. The addition condensation product according to claim 1, wherein the carbonyl compound is an aldehyde compound or a ketone compound.

4. The addition condensation product according to claim 1, wherein
   the aromatic compound is a compound represented by general formula (1) below and the carbonyl compound is an aldehyde compound represented by general formula (2) below:

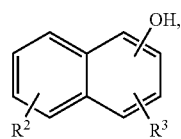

(1)

(2)

where $R^1$, $R^2$, and $R^3$ each in the general formulae (1) and (2) each represent a hydrogen atom or a hydrocarbon group.

5. The addition condensation product according to claim 1, wherein the aromatic compound is a-naphthol, and the carbonyl compound is formaldehyde.

6. A production method of an addition condensation product, the method comprising:
   a step of mixing an aromatic compound, a carbonyl compound, and a catalyst in a reaction solvent such that an addition condensation reaction of the aromatic compound and the carbonyl compound is conducted to obtain the addition condensation product of the aromatic compound and the carbonyl compound, wherein the addition condensation product includes an aromatic compound dimer in which two composition units derived from the aromatic compounds are bonded via one composition unit derived from the carbonyl compound and an aromatic compound multimer in which each of three or more composition units derived from the aromatic compounds is bonded via one composition unit derived from the carbonyl compound, a ratio of the aromatic compound dimer to the aromatic compound multimer is in a range of 1:75 to 1:1,000, and the addition condensation product is a reaction product of the carbonyl compound in a range of 0.1 to 0.999 moles relative to 1 mole of the aromatic compound.

7. The production method of the addition condensation product according to claim 6, wherein the aromatic compound is a-naphthol, the carbonyl compound is formaldehyde, and the catalyst is an alkali metal hydroxide.

8. A polymerization vessel for polymerization of a monomer, wherein the polymerization vessel has an inner surface that is coated with a solution of the addition condensation product according to claim 1, wherein said coated inner surface comes into contact with the monomer.

9. The polymerization vessel according to claim 8, further comprising:

a reflux condenser to condense the monomer during polymerization.

10. The polymerization vessel according to claim 8, wherein the monomer is a monomer having an ethylenic unsaturated group.

11. The polymerization vessel according to claim 10, wherein the monomer having an ethylenic unsaturated group is vinyl chloride.

12. A production method of a polymer wherein the monomer is polymerized in the polymerization vessel according to claim 8.

13. A polymer scale adhesion preventive agent, comprising:

the addition condensation product according to claim 1.

14. The addition condensation product according to claim 1, wherein the addition condensation product is a reaction product of the carbonyl compound in a range of 0.5 to 0.99 moles relative to 1 mole of the aromatic compound.

15. The addition condensation product according to claim 14, wherein the aromatic compound is a naphthol.

16. The addition condensation product according to claim 14, wherein the carbonyl compound is formaldehyde.

17. The addition condensation product according to claim 14, wherein the aromatic compound is a-naphthol, and the carbonyl compound is formaldehyde.

18. The addition condensation product according to claim 14, wherein the carbonyl compound is a ketone compound.

19. The addition condensation product according to claim 1, wherein the carbonyl compound is a ketone compound.

20. The addition condensation product according to claim 1, wherein the ratio of the aromatic compound dimer to the aromatic compound multimer is in a range of 1:80 to 1:400.

\* \* \* \* \*